United States Patent [19]

John et al.

[11] Patent Number: 4,699,651

[45] Date of Patent: Oct. 13, 1987

[54] USE OF CERTAIN CINNOLINE-4-CARBOXYLIC ACIDS AND CONGENERS THEREOF FOR CONTROLLING THE GROWTH OF UNWANTED PLANTS

[75] Inventors: William W. John; Herbert Estreicher; Samuel B. Soloway, all of Modesto, Calif.

[73] Assignee: E. I. Du Pont de Nemours and Company, Wilmington, Del.

[21] Appl. No.: 765,630

[22] Filed: Aug. 15, 1985

Related U.S. Application Data

[63] Continuation-in-part of Ser. No. 639,985, Aug. 13, 1984, abandoned, which is a continuation-in-part of Ser. No. 516,076, Jul. 22, 1983, abandoned.

[51] Int. Cl.$^4$ ............................................. A01N 43/58
[52] U.S. Cl. .......................................... 71/92; 71/86
[58] Field of Search ....................... 71/92, 86; 544/235

[56] References Cited

U.S. PATENT DOCUMENTS

| | | | |
|---|---|---|---|
| 2,940,844 | 6/1960 | Gysin et al. ............................. | 71/92 |
| 3,419,381 | 12/1968 | Desmoras et al. ....................... | 71/92 |
| 3,459,759 | 8/1969 | Röchling et al. ........................ | 71/92 |
| 3,657,241 | 4/1972 | Kurihara ................................. | 71/92 |
| 3,749,718 | 7/1973 | Ailman .................................... | 71/92 |
| 3,883,550 | 5/1975 | Goddard ................................. | 71/92 |
| 4,118,217 | 10/1978 | Oestreicher et al. ................... | 71/92 |

FOREIGN PATENT DOCUMENTS

| | | | |
|---|---|---|---|
| 0220776 | 6/1956 | Australia ................................. | 71/92 |
| 0049029 | 6/1981 | Australia .............................. | 544/235 |

OTHER PUBLICATIONS

Bidlack et al., "Method for Selective Control of Annual Grass," Defensive Publication T893,002, 983 O.G. 401 (12–1971).

Jacobs et al., "4–Substituted Cinnoline Derivatives," Chem. Abstr. 40:5749–50 (1946).

Castle et al., "Cinnoline Chemistry VI, etc.," Chem. Abstr. 55:27355g (1961).

*Primary Examiner*—Glennon H. Hollrah
*Assistant Examiner*—P. Morris

[57] ABSTRACT

The growth of unwanted plants is controlled by certain cinnoline-4-carboxylic acids and congeners thereof.

1 Claim, No Drawings

USE OF CERTAIN CINNOLINE-4-CARBOXYLIC ACIDS AND CONGENERS THEREOF FOR CONTROLLING THE GROWTH OF UNWANTED PLANTS

This application is a continuation-in-part of copending application Ser. No. 639,985, filed on Aug. 13, 1984, now abandoned which was a continuation-in-part of application Ser. No. 516,076, filed on July 22, 1983, abandoned.

DESCRIPTION OF THE INVENTION

It has been found that the growth of certain plants is adversely affected by cinnoline-4-carboxylic acid and its congeners, of the formula:

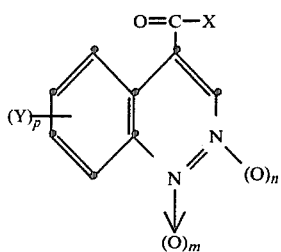

wherein m is zero or one, n is zero or one, with the proviso that at least one of m and n is zero, p is zero, one or two, with the proviso that when p is two, one of Y is methyl or ethyl, X is one of the moieties: —$NH_2$, —$NHNH_2$, —NHOH and —O—R, wherein R is
(a) hydrogen;
(b) alkyl of one to ten carbon atoms;
(c) alkyl of one to ten carbon atoms substituted by one of cyano, alkanoyl, carboxy, alkoxycarbonyl, aminocarbonyl, mono- and dialkylaminocarbonyl, benzyloxycarbonyl, alkylthiocarbonyl, alko-nyl and alkynyl of two to four carbon atoms, cycloalkyl of three to six carbon atoms, dialkoxyphosphinyl, tetrahydrofuranyl, tetrahydropyranyl, dioxanyl, dioxolanyl, pyridinyl, pyridinyl-N-oxide, and optionally substituted phenyl;
(d) alkyl of two to ten carbon atoms substituted by one to three halogen atoms (bromine, chlorine, fluorine); one of alkylthio, alkanoyloxy, mono- and dialkylamino, moieties of the formula —(—O—R$^1$—)$_q$—O—R$^2$ (in which R$^1$ is alkylene of one to four carbon atoms, R$^2$ is hydrogen or alkyl of one to six carbon atoms and 8 is one, two, three or four), or one to four of hydroxy and alkoxy, with the proviso that in this substituted alkyl moiety the carbon atom bonded to the indicated oxygen atom is unsubstituted (—$CH_2$—);
(e) cycloalkyl of three to six carbon atoms;
(f) optionally substituted phenyl;
(g) pyridinyl;
(h) heterocyclyl of five or six atoms containing one or two oxygen atoms bonded only to carbon therein;
and Y is
(a) alkyl of one to ten carbon atoms;
(b) alkyl of one to ten carbon atoms substituted by one of fluorine, cyano, carboxy, alkenyl of two to four carbon atoms, benzyl, alkoxycarbonyl, alkylthio, alkylsulfinyl, alkoxy and phenoxy, and salts of those compounds wherein R is hydrogen or X is —NHOH.

In these compounds, the (substituted) alkyl moiety may be either straight-chain or branched-chain. Suitable substituents on any phenyl moiety include mono- and polyhalo, or one or two of mono- and polyhaloalkyl, carboxy, nitro, alkoxycarbonyl, alkyl, alkoxy and alkylthio. In the substituent moieties, each alkyl moiety suitably contains from one to four carbon atoms, and is either straight-chain or branched-chain.

The contemplated salts are those of alkali metals, alkaline earth metals, amines and ammonia. Suitable amine salts are those of mono-, di- and tri-alkyl- and -alkanol- amines wherein each alkyl moiety contains up to twenty carbon atoms.

The subgenus of the compounds of Formula I wherein p is one or two and a substituent Y is bonded to the carbon atom in the 8-position is preferred, since compounds of that subgenus appear to have the widest spectrum of phytotoxic activity—i.e., the number of different varieties of plants that are adversely affected by the compound.

The preparation, isolation and testing of typical individual species of the compounds of Formula I are described in the examples, following. The class of compounds is further illustrated and exemplified by the following further individual species, all of which are specifically contemplated in this invention. In the interest of brevity, and clarity, and to avoid repetition of sometimes long chemical names, these species will be identified in terms of Formula I and the symbols used therein. The following are species of the subgenus wherein X is $CH_3O$—, m and n each is zero:

| Species No. | Y (number indicates position on ring) |
|---|---|
| 77 | 5-methyl- |
| 78 | 8-propyl- |
| 79 | 8-butyl- |
| 80 | 8-(1,1-dimethylethyl)- |
| 81 | 8-(ethenyl)- |
| 82 | 8-(1-methylethenyl)- |
| 83 | 8-(cyanomethyl)- |
| 84 | 8-(carboxymethyl)- |
| 85 | 8-(methoxycarbonylmethyl)- |
| 86 | 8-(methylthiomethyl)- |
| 87 | 8-(methylsulfonylmethyl)- |
| 88 | 8-(methoxymethyl)- |
| 89 | 8-(phenoxymethyl)- |
| 90 | 8-(difluoromethyl) |
| 91 | 8-(1-cyano-1-methylethyl)- |
| 92 | 8-(1-carboxy-1-methylethyl)- |
| 93 | 8-(1-(methylthio)-1-methylethyl)- |
| 94 | 8(1-methylsulfonyl-1-methylethyl)- |
| 95 | 5,8-dimethyl |
| 96 | 8-cyclopropyl- |
| 97 | 8-(1-methylcyclopropyl)- |
| 98 | 5-methyl-8-(1-methylethyl)- |
| 99 | 5-(1-methylethyl)-8-(methyl)- |
| 100 | 8-(1-propenyl)- |
| 101 | 8-(2-methyl-1-propenyl)- |
| 102 | 8-benzyl |
| 103 | 6,8-dimethyl- |
| 104 | 5,6-dimethyl- |
| 105 | 5,7-dimethyl- |

The following are species wherein p is one:

| Species No. | X | n | m | (Y)$_p$ (number indicates position on ring) |
|---|---|---|---|---|
| 106 | —O—2-(2-(2-methoxy-ethoxy)ethoxy)ethyl | 0 | 0 | 8-methyl |
| 107 | —O—2-(2-(2-(2-hydroxy-ethoxy)ethoxy)ethoxy)ethyl | 0 | 0 | 8-ethyl |
| 108 | —O—(1,3-dioxolan-4-yl)methyl | 0 | 0 | 8-ethyl |
| 109 | —O—2-(2-hydroxy-1-methyl-ethoxy)propyl | 0 | 0 | 8-ethyl |
| 110 | —O—(1,3-dioxolan-2-yl)methyl | 0 | 0 | 8-ethyl |
| 111 | —O—2-(methoxy)ethyl | 0 | 0 | 8-ethyl |
| 112 | —O—pentyl | 1 | 0 | 8-methyl |
| 113 | —O—butyl | 1 | 0 | 8-methyl |
| 114 | —O—butyl | 1 | 0 | 8-ethyl |
| 115 | —O—propyl | 1 | 0 | 8-(1-methylethyl) |

The following are species of the subgenus wherein p is zero:

| Species No. | X | n | m |
|---|---|---|---|
| 116 | —O—butyl | 1 | 0 |
| 117 | —O—butyl | 0 | 1 |
| 118 | —O—pentyl | 1 | 0 |
| 119 | —O—pentyl | 0 | 1 |
| 120 | —O—hexyl | 1 | 0 |
| 121 | —O—hexyl | 0 | 1 |
| 122 | —O—(3-methylbutyl) | 1 | 0 |
| 123 | —O—(3-methylbutyl) | 0 | 1 |

Cinnoline-4-carboxylic acid is a known compound, as is its ethyl ester: Jacobs, T. L. et. al., J. Am. Chem. Soc. 1946, 68, 1310-13. The acid currently is available commercially. As shown in that reference, esters can be prepared by conventional procedures; as can salts of the acid and of the hydroxamic acid (X=—NHOH). Three preparative routes are illustrated in the examples set out hereinafter. Examples 4 and 6-13 show preparation of esters by treating the acid with oxalyl chloride, and treating the resulting acid chloride with the appropriate alcohol or phenol. Examples 5 and 14-26 show preparation of esters by treating the acid with CDII (carbonyldiimidazole) and treating the resulting cinnoline-4-imidazolide with the appropriate alcohol or phenol. Example 32 shows preparation of an ester by treating the acid with an appropriate halide in the presence of DBU (1,8-diazabicyclo[5.4.0]undec-7-eue). Example 27 shows preparation of the amide (X=—NH$_2$). Example 28 shows preparation of the hydroxamic acid (X=—N-HOH). Examples 31, 38-40 and 75 shows preparation of N-oxides (m or n=1). Examples 2 and 29 show preparation of salts of the acid and hydroxamic acid, respectively.

Cinnoline-4-carboxylic acid and substituted congeners also can be prepared by a route different from that of Jacobs, et al. In this new route, 4-methylcinnoline, or the appropriately-substituted congener, is converted to the corresponding 4-(trichloromethyl)cinnoline, which is converted to the desired acid. The method for converting the 4-methylcinnoline to the corresponding 4-(trichloromethyl)cinnoline is the subject of application Ser. No. 646,674, filed on Sept. 4, 1984. The cinnoline-4-carboxylic acid is prepared by treating the appropriate 4-(trichloromethyl)cinnoline with sulfuric acid, as shown in Examples 41, 49 and 51, hereinafter.

Conversion of the trichloromethyl cinnoline to the acid is effected by slowly dissolving the cinnoline in concentrated sulfuric acid, and heating the solution at a temperature of about 125°-150° C. for a sufficient time to effect completion of the reaction—usually of the order of 15-25 hours. The reaction mixture is quenched with ice, then made basic with an aqueous solution of a metal base, such as sodium hydroxide, or concentrated ammonium hydroxide, and the resulting mixture is washed with a solvent, such as methylene chloride, to remove any unreacted cinnoline, and filtered. The filtrate is carefully acidified to give the acid, hydrochloric acid being a suitable acidifying agent.

Details of the method for preparing the 4-(trichloromethyl)cinnoline precursors, and methods for preparing their necessary precursors are set forth in application Ser. No. 646,674, and those disclosures are incorporated herein by this reference thereto. Briefly, the cinnoline precursors

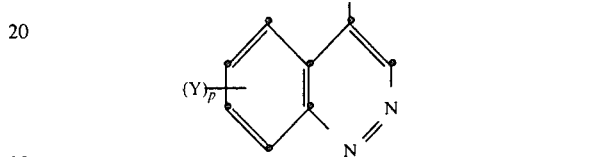

(II)

wherein X=—CCl$_3$, are prepared by treating the corresponding 4-methylcinnoline (X=methyl) with a stoichiometrically moderate excess of sodium hypochlorite in liquid medium comprising essentially water and a polar, water-miscible inert organic liquid as co-solvent, the sodium hypochlorite concentration being from eight to fifteen percent by weight of the medium, and the initial pH of the medium being from about 12 to about 14. The treatment is carried out at about room temperature (15° C.-30° C.) and the reaction ordinarily requires from about 5-60 hours. Conveniently, the 4-methycinnoline is dissolved in the co-solvent, and the solution is mixed with the aqueous sodium hypochlorite solution, Suitable co-solvents include dioxane, diglyme, sulfolane and dimethylformamide.

Examples 53 and 54, hereinafter, exemplify a further sequence of procedures whereby compounds of Formula I can be prepared.

Compounds 77-82, and 95-102 can be prepared from known substituted anilines, or substituted anilines that are readily prepared by conventional procedures. Compound 83 can be prepared by treating the 8-(chloromethyl) species with potassium cyanide in dimethylformamide at 80°-120° C. The 8-chloromethyl species can be prepared by treatment of Compound 50 with a chlorinating agent such as N-chlorosuccinimide of sulfuryl chloride in an appropriate solvent such as carbon tetrachloride or dichloroethane in the presence of a free radical initiator such as benzoyl peroxide or azo-isobisbutyronitrile (AIRN) at the boiling point of the solvent used. Compound 84 can be prepared by hydrolysis of Compound 83 with sulfuric acid-water (1:1 v/v) at 95°-100° C. for 24-48 hours; re-esterification as described in Example 54 gives Compound 85. Compound 86 can be prepared by treating the 8-(chloromethyl) species with sodium mercaptide in hot dimethylformamide. Compound 87 can be prepared by oxidizing Compound 86 with aqueous potassium permanganate. Compound 88 can be prepared by treating the 8-(chloromethyl) species with sodium methoxide in boiling methanol. Compound 89 can be prepared by treating the 8-(chloromethyl) species with sodium phenoxide in dimethylformamide at 80° C. Compound 90 can be prepared by treating compound 50 with two equivalents of N-bromosuccinimide in an appropriate solvent such as carbon tetrachloride or dichloroethane in the presence of a free radical initiator such as benzoyl peroxide at the boiling point of the solvent to produce methyl 8-(dibromomethyl)cinnoline-4-carboxylate, which upon treatment with silver nitrate in aqueous dioxane gives methyl 8-formylcinnoline-4-carboxylate, which is converted to 90 by treating it with diethylaminosulfur triflouride in a freon solvent, analogous to the procedure of W. J. Middleton, Journal of Organic Chemistry, volume 40, pages 574–578 (1975). Compound 91, 92, 93, and 94 can be prepared from Compound 57 by procedures analogous to those described above for the preparation of Compounds 83–87. Compound 103 can be prepared from 3,5-dimethylanthranilic acid by the procedures described in Example 1. Compound 104 can be preapared from 3,4-demethylaniline, and Compound 105 can be prepared from 3,5-dimethylaniline, by the procedures described in Examples 53 and 54 for preparing Compound 54 from 2-ethylaniline. Compounds 106 through 123 can be prepared by analogous procedures.

The following examples describe the preparation, isolation and physical properties of typical individual species of the compounds of Formula I, in particular instances, in each case, the identity of each product, and each of any intermediate involved, was confirmed by appropriate chemical and spectral analyses.

EXAMPLE 1

Cinnoline-4-carboxylic Acid (1)

Jacobs et al., a solid, m.p.: 196° C. (with decomposition).

The diisopropylamine and dicyclohexylamine salts of 1 were prepared by mixing, in each case, an excess of the amine with 1, then distilling the excess amine.

EXAMPLE 2

Potassium Cinnoline-4-carboxylate (2)

5.10 g of (1) was added over 30 minutes to a vigorously stirred solution of 2.02 g of potassium carbonate in 25 ml of water, at room temperature. The resulting mixture was stirred for one hour at room temperature, then treated with charcoal, and after filtration the water was evaporated. The residue was azeotropically distilled with toluene and dried at 70° C. under reduced pressure, to give 2, as a light tan powder, m.p.: above 280° C.

EXAMPLE 3

Ethyl Cinnoline-4-carboxylate (3)

Jacobs et al., a solid, m.p.: 48.5°–49.5° C.

EXAMPLE 4

Methyl Cinnoline-4-carboxylate (4)

A solution of 0.64 g of oxalyl chloride in 5 ml of dry toluene was added over 5 minutes to a stirred suspension of 0.98 g of 2 in 10 ml of dry toluene, at 0° C. The resulting mixture was stirred for 20 minutes at 0° C., for 30 minutes at room temperature, and for one hour at 80° C. The mixture was cooled and added in portions over 5 minutes to a stirred ice cold mixture of 0.4 g of pyridine, 0.32 g of methanol and 10 ml of dry toluene. The resulting mixture was held overnight at room temperature, then stripped in a rotary evaporator, and the residue was chromatographed over silica gel, using 5% ethyl acetate/methylene chloride mixture as eluent, to give 4, as yellow crystals, m.p.: 57°–58° C.

EXAMPLE 5 n-Propyl Cinnoline-4-carboxylate (5)

A suspension of 870 mg of 1, and 850 mg of carbonyidimidazole (CDII) in 30 ml of tetrahydrofuran (THF) was stirred at room temperature until $CO_2$ evolution ceased (ca. 30 minutes). After being stirred for 2 hours, the resulting mixture was treated with 320 mg of dry nypropanol and 3 drops of a 0.1 M solution of sodium imidazole in THE. The mixture was held at room temperature overnight, then the solvent was evaporated and the residue was partitioned between water and ether. The etheral extract was washed with saturated sodium bicarbonate solution, then with brine, then dried ($MgSO_4$) and stripped in a rotary evaporator. The residue was chromatographed over silica gel, using a 1:1 v:v mixture of cyclohexane and ethyl acetate as eluent, to give 5, as a yellow oil.

EXAMPLES 6–9

By the procedures described in Example 4, the following esters of cinnoline-4-carboxylic acid were prepared from the corresponding alcohols:
n-butyl ester (6), as a yellow oil;
sec-butyl ester (7), as a yellow oil;
lert-butyl ester (8), as a solid, m.p.: 76°–77° C.
benzyl ester (9), as yellow crystals, m.p.: 78°–79° C.

EXAMPLE 10–13

By the procedures described in Example 4, the following esters of cinnoline-4-carboxylic acid were prepared from the corresponding phenols:
phenyl ester (10), as yellow crystals, m.p.: 116°–117° C.;
4-methylphenyl ester (11), as a yellow solid, m.p.: 102°–103° C.;
3-methylphenyl ester (12), as yellow crystals, m.p.: 86°–88° C.;
4-chlorophenyl ester (13), as a yellow solid, m.p.: 143°–145° C.

EXAMPLES 14–26

The following esters were prepared from 1 and the corresponding phenols or alcohols by the procedures described in Example 5, except that in some cases it was not necessary to include the sodium imidazole:
4-(methylthio)phenyl ester (14), as a yellow solid, m.p.: 127° C.;
3-fluorophenyl ester (15), as yellow crystals, m.p.: 92°–93° C.;
cyclohexyl ester (16), as yellow crystals, m.p.: 89°–90° C;
2,2,2-trichloroethyl ester (17), as a yellow oil;
cyclopropylmethyl ester (18), as a yellow oil;
(benzyloxycarbonyl)methyl ester (19), as a yellow oil;
2-pyridinylmethyl ester (20), as yellow crystals, m.p.: 86° C.;
2-(dimethylamino)ethyl ester (21), as yellow crystals, m.p.: not determined;
(tetrahydropyran-2-yl)methyl ester (22), as a yellow oil;
2-(diethoxy phosphinyl)methyl ester, (23), as a yellow oil;
tetrahydrofuran-3-yl ester (24), as a yellow oil;
2,3-(dihydroxy)propyl ester (25), as a viscous yellow oil;

3-pyridinyl ester oxide (26), as yellow crystals, m.p.; 153°–154° C. (with decomposition).

EXAMPLE 27

Cinnoline-4-carboxamide (27)

A solution of 50.0 g of o-isopropenylaniline (Aldtich) in 440 ml of 2 N hydrochloric acid was treated with 86 ml of 12 N hydrochloric acid at 20° C. The resulting mixture was extracted with ether to remove a small amount of an insoluble oil. The aqueous phase was cooled to 0° C. and treared with 24.5 g of sodium nitrite, in portions, over 2 hours, at 0°–5° C. The resulting mixture was stirred for 30 minutes at 0° C., warmed to room temperature, heated to 60° C., and then held at room temperature over a weekend. It was neutralized with sodium bicarbonate, made basic with 50% sodium hydroxide solution, and extracted with ether. The extract was washed with brine, dried (MgSO4), charcoaled, filtered and stripped of solvent. The residue was recrystallized from hexane to give 4-methylcinnoline (27A), as a solid, m.p.: 70°–72° C.

A solution of 1.44 g of 27A in 3 ml of absolute ethanol was added drop-by-drop over 3 minutes to 3.4 ml of stirred absolute ethanol containing 0.9 g of anhydrous hydrogen chloride, at 0° C. The resulting mixture was stirred for 30 minutes, then a solution of 1.03 g of butyl nitrite in 2 ml of absolute ethanol was added drop-by-drop over 3 minutes at 0° C. The mixture was stirred for 30 minutes at 0° C., for 4 hours at room temperature, then stored in a refrigerator overnight. A precipitated solid was collected, washed with a small amount of water, mixed with a saturated potassium bicarbonate solution, and filtered. Recrystallization from water gave 4-(hydroximinomethyl)cinnoline (27B), as a solid, m.p.: 223° C. (with decomposition).

A stirred solution of 0.173 g of 27B in 5 ml of acetic anhydride was refluxed overnight under nitrogen. The mixture was stripped under reduced pressure, and the residue was recrystallized from hexane to give cinnoline-4-carbonitrile (27C), as a yellow crystalline solid, m.p.: 140° C.

0.76 g of hydroxylamine hydrochloride was added to a stirred solution of 0.72 g of 85% aqueous potassium hydroxide in 25 ml of absolute ethanol at room temperature. The mixture was stirred at room temperature for 20 minutes, then 1.55 g of 27C was added and the mixture was heated at reflux for 3 hours, held overnight at room temperature, and filtered. The filtrate was stripped of solvent to give a dark oil, from which a yellow solid precipitated on standing. The solid was separated, and stirred in hot ethyl acetate. The resulting mixture was filtered, the solvent was stripped from the filtrate and the residue was recrystallized from ethanol to give 27, as a yellow solid, m.p.: 223° C.

EXAMPLE 28

Cinnoline-4-hydroxamic acid (28)

A solution of 0.067 g of sodium metal in 2.5 ml of dry methanol was added to a solution of 0.20 g of hydroxylanine hydrochloride in 5 ml of dry methanol, at 10°–20° C. The mixture then was treated with 0.50 g of 4 and then with a solution of 0.061 g of sodium metal in 2.4 ml of dry methanol, and the resuiting mixture was stirred overnight at room temperature. This mixture then was neutralized with 3 N hydrochloric acid solution and filtered. The filtrate was stripped in a rotary evaporator and the residue was recrystallized from water to give 28, as tan crystals, m.p.: 165° C. (with decomposition).

EXAMPLE 29

Potassium salt (29) of 28

0.19 g of 28 was added to a slurry of 0.07 g of potassium carbonate in 10 ml of methanol at room temperature. The resulting mixture was stirred at room temperature for 2 hours, then stripped to dryness to give 29, as a solid, m.p.: 191°–192° C. (with decomposition).

EXAMPLE 30

Hydrazide of 1

2.0 g of 1 was added to a solution of 1.87 g of CDII in 250 ml of anhydrous THF in an argon atmosphere, the resulting mixture was stirred at room temperature for 4 hours, 0.7 g of hydrazine hydrate (as an 85% solution in water) was added over one minute to the stirred mixture. The mixture was stirred for a further 48 hours, then was stripped of solvent. The residue was dried by mixing it with 75 ml of absolute alcohol, then stripping the alcohol. The resulting residue was taken up in ethyl acetate, the solution was cooled and filtered to give (30), as a yellow solid, m.p.: 172°–174° C.

EXAMPLE 31

The 2-N-oxide (31) of 8

0.2 g of m-chloroperoxybenzoic acid (MCPBA) was added to a cold solution of 0.2 g 8 in 20 ml of methylene chloride. The resulting mixture was held in a refrigerator (2° C.) overnight, then treated with a 10% aqueous solution of sodium sulfite, washed with water, then brine, dried and stripped in a rotary evaporator. The residue was flash chromatographed on silica gel using 5% ethyl acetate/methylene dichloride mixture as eluent. Work-up gave 31, as a solid, m.p.; 146°–147° C.

EXAMPLE 32 1

1-(Ethoxycarbonyl)ethyl Cinnoline-4-carboxylate (32)

A solution of 0.75 ml of 1,8-diazabicyclo[5.4.0]undec-7-ene (DBU) in 20 ml of benzene was added to a stirred suspension of 0.87 g of 1 in 30 ml of benzene at room temperature. After one hour of stirring, 1.36 g of ethyl 2-bromopropionate was added and the mixture was heated at reflux for 6 hours. The mixture was cooled, diluted with 25 ml of benzene, washed with water, 1 N aqueous sodium bicarbonate, and brine. It then was dried (MgSO4), the solvent was evaporated and the residue was chromatographed on silica gel, using a 1:1 v:v mixture of cyclohexane and ethyl acetate as eluent, to give 32, as a yellow oil.

EXAMPLES 33–37

The following esters were prepared from 1 and the corresponding alcohols by the procedures described in Example 32:

cyanomethyl ester (33), as yellow crystals, m.p.: 133°–134° C.;
2,2-(dimethoxy)ethyl ester (34), as yellow crystals, m.p.: 65°–67° C.;
(aminocarbonyl)methyl ester (35), as yellow crystals, m.p.: 205°–206° C.;
Terr-butoxycarbonylmethyl ester (35), as a yellow solid, m.p.: 80°–81° C.;
1-(methoxycarbonyl)methyl ester (37), as a yellow solid m.p.: 85° C.

EXAMPLES 38 and 39

N-oxides of 4

3.3 g of 80% MCPBA was added in portions (over one hour) to a stirred solution of 2.67 g of 4 in 100 ml of dry methylene chloride, at 0° C. The mixture then was stirred at 0° C. for 2.5 hours and held in a refrigerator overnight. The excess peracid was decomposed with 10% aqueous sodium thiosulfate, the mixture was washed, successively, with water, saturated sodium bicarbonate solution and brine, dried (MgSO$_4$) and stripped of solvent. The residue was flash chromatographed on silica using a 3:97 v:v mixture of ethyl acetate and methylene chloride as eluent. On workup, two solids were obtained; the first was the 1-N-oxide (38) of 4, m.p.: 109°–110° C.; the second was the 2-N-oxide (39) of 4, m.p.: 111°–112° C.

EXAMPLE 40

The free acid (40) of 39 was prepared by adding 10 ml of 25% aqueous sodium hydroxide solution to a solution of 0.40 g of 39 in 20 ml of methanol at 20°–25° C., and stirring the resulting mixture for 20 minutes. The mixture then was acidified with hydrochloric acid, stripped of most of the methanol and extracted with ethyl acetate. The extract was stripped of solvent and the residue was recrystallized from ethanol to give 40, as a solid, m.p.: 228° C., with decomposition.

EXAMPLE 41

Cinnoline-4-carboxylic Acid (1)—Alternative Preparation 1.23 liters of a 10.5% solution of sodium hypochlorite in water, pH=2.7, was added to a stirred solution of 50.0 g of 19A in 88 ml of dioxane at room temperature and the resulting mixture was stirred for 60 hours at room temperature. The precipitated solid was collected, washed with water, and dried under reduced pressure, to give 4-(trichloromethyl)cinnoline (41A), as a pale green solid, m.p.: 137° C.

14.0 g of 41A was slowly dissolved in 18 ml of 95% sulfuric acid. The mixture was heated at 135°–140° C. for 20 hours, cooled, poured onto 60 g of ice and made basic with 30% aqueous sodium hydroxide. The mixture was washed with methylene chloride and filtered. The filtrate was cooled to ice-bath temperature and carefully acidified to pH=1.5-2 with concentrated hydrochloric acid. The solid product was collected, washed with a small amount of cold water and dried under reduced pressure to give 1 as a solid, m.p.: 176°–178° C. (with decomposition), identical in all respects to a commercial sample.

EXAMPLE 42

2-(2-ethoxyethoxy)ethyl cinnoline-4-carboxylate (42)

1.07 g of CDIT was added to a mixture of 1.04 g of 1 in 70 ml of dry THF under nitrogen, the mixture was stirred at room temperature for 4 hours, 1.6 g of 2-(2-ethoxyethoxy)ethanol and 0.032 g of sodium methoxide were added and the mixture was stirred at room temperature over a weekend. Then the solvent was stripped, and the residue was dissolved in methylene chloride. The solution was washed with water, dried (MgSO$_4$) and stripped of solvent. The residue was flash-chromatographed on silica gel, using a 1:4 v:v mixture of ethyl acetate and methylene chloride as eluent, to give 42, as a yellow oil.

EXAMPLES 43–48

The following esters were prepared from 1 and the corresponding alcohols by the procedures described in Example 42:

(1,3 dioxan-5-yl) ester (43), as a yellow solid, m.p.: 131°–132° C.;
oxiranylmethyl ester (44), as a yellow solid, m.p.: 87°–88° C.;
(1,3-dioxolan-4-yl)methyl ester (45), as a yellow solid, m.p.: 75°–76° C.;
2-(2-methoxyethoxy)ethyl ester (46), as a yellow oil;
2-(methoxy)ethyl ester (47), as a yellow solid, m.p.: 70°–71° C.;
2-(ethoxy)ethyl ester (48), as a yellow oil.

EXAMPLE 49

8-Methyleinnoline-4-carboxylic Acid (49).

A solution of 60.8 g of 2-amino-3-methylbenzoic acid in 900 ml of dry methanol was saturated with anhydrous hydrogen chloride at 0°–10° C., then allowed to stand at room temperature overnight. Then it was refluxed for one hour, cooled to 5° C., resaturated with anhydrous hydrogen chloride, held overnight at room temperature and stripped of solvent. The residue was made neutral with saturated aqueous sodium bicarbonate solution, and extracted with methylene chloride. The extract phase was washed with saturated aqueous sodium bicarbonate solution, dried (MgSO$_4$), filtered and stripped of solvent. The residue was distilled in a kugelrohr apparatus to give methyl 2-amino-3-methylbenzoate (49A), b.p.: 100°–105° C. (1Torr.).

130 ml of a 3 M solution of methyl magnesium chloride in 130 ml of THF was added drop-by-drop to a stirred solution of 11 g of 49A in 70 ml of dry ether at 0°–5° C. in a nitrogen atmosphere. The resulting mixture was allowed to warm to room temperature and stirred at reflux (40° C.) for 5 hours and held overnight at room temperature. The mixture then was quenched in a mixture of 48 g of ammonium chloride and 350 g of ice. 30 ml of 3 N hydrochloric acid was added, the solvents were evaporated, and the residue was extracted with ether. The extract phase was washed with water, then brine, dried (K$_2$CO$_3$), filtered and stripped of solvent. The residue was recrystallized from hexane to give (2-amino-3-methylphenyl)dimethylcarbinol (49B), as colorless needles, m.p.: 78°–79° C.

49B was dissolved in 60 ml of toluene containing 5 mg of iodine, and the mixture was refluxed overnight. The solvent was evaporated and the residue was distilled in a short-path bantumware apparatus to give 2-(2-amino-3-methylphenyl)propene (49C), as a colorless oil, b.p.: 82°–85° C. (2 Torr.).

6.9 g of 49C was added to 55 ml of 2 N hydrochloric acid at 10° C. Then 11 ml of 12 N hydrochloric acid was added, the mixture was cooled to 0° C., treated with 3.1 g of sodium nitrite, in portions over a two-hour period. The mixture was allowed to warm slowly to room temperature, then was heated to 50° C. and left to stand over a weekend at room temperature. The mixture was made basic with solid sodium carbonate, and extracted with ether. The extract phase was washed with water, then brine, dried (MgSO$_4$), filtered and stripped of solvent. The residue was flash chromatographed over silica gel, using a 2:3 v:v mixture of ethyl acetate and methylene chloride as eluent. The solvent was evaporated to give 4,8-diemthylcinnoline (49D), as a solid, m.p.: 89°–90° C.

45 ml of commercial bleach (about 10% sodium hypochlorite, pH=12) was added to a stirred solution of 1.9 g of 49D in 5 ml of dioxane, at room temperature. The mixture was stirred at room temperature for 2 hours, 3 ml of dioxane was added and the mixture was stirred for 4½ days at room temperature. Then the mixture was diluted with water and filtered. The solid was washed with water and dissolved in methylene chloride. The solution was dried ($MgSO_4$), filtered and the solvent was evaporated to give 8-methyl-4-(trichloromethyl)cinnoline (49E), as a yellow solid, m.p.: 135°–357° C., with decomposition.

1.25 g of 49E was slowly added (over 5 minutes) to 2 ml of concentrated sulfuric acid. The resulting solution was stirred at 135°–140° C. overnight, then quenched on 6 g of ice. The mixture was made basic with 50% aqueous sodium hydroxide solution, and extracted with methylene chloride and ethyl acerate. The aqueous phase was carefully acidified with 12 N hydrochloric acid, and filtered. The solid was dried by azeotroping with methanol and toluene. The dried solid was dissolved in methanol, the solution was filtered, then stripped of solvent, to give 49, as a solid, m.p.: 181°–182° C., with decomposition.

EXAMPLE 50

Methyl 8-Methylcinnoline-4-carboxylate (50)

A solution of 0.65 g of 49 in 20 ml of dry THF was refluxed in a nitrogen atmosphere, then cooled to room temperature and 0.62 g of CDII was added. The mixture was stirred for 7 hours at room temperature, then a suspension of 0.1 equivalent of sodium methoxide in 2 equivalents of methanol was added and the mixture was stirred in a nitrogen atmosphere overnight. The THF was evaporated, the residue was diluted with water and extracted with methylene chloride. The extract phase was washed with saturated sodium bicarbonate solution, then brine, dried ($MgSO_4$), filtered and stripped of solvent to give 50, as a solid, m.p.: 90°–91° C.

EXAMPLE 51

6-Methylcinnoline-4-carboxylic acid (51)

51 was prepared, as a tan solid, m.p.: 179°–180° C., from 2-amino-5-methylbenzoic acid, by the respective procedures described in Example 49 for preparing 49 from 2-amino-3-methylbenzoic acid: via methyl 2-amino-5-methylbenzoate (a solid, m.p.: 62°–63° C.), (2-amino-5-methylphenyl)dimethylcarbinol (an oil, b.p.: 100° C./0.1 Torr.), 2-(2-amino-5-methylphenyl)propene (a liquid, b.p.: 87°–90° C./0.5 Torr.), 4,6-dimethylcinnoline (a solid, m.p.: 75°–76° C.), and 6-methyl-4-(trichloromethyl)cinnoline (green crystals, m.p.: 132°–133° C., with decomposition).

EXAMPLE 52

Methyl 6-methylcinnoline-4-carboxylate (52), was prepared, as a yellow solid, m.p.: 73°–74° C., from 51 by the procedures described in Example 50 for preparing 50 from 49.

EXAMPLE 53

8-Ethylcinnoline-4-carboxylic Acid (53)

97.0 g of 2-ethylaniline was mixed with 200 ml of 12 N hydrochloric acid, then 400 g at crushed ice was added and the mixture was cooled to −10° C. Then a solution of 56.4 g of sodium nitrite in 135 ml of water was added to the stirred mixture, over a period of about 35 minutes, at −10° C. to 2° C., followed by 3 g of urea. The mixture was stirred for 10 minutes, then was filtered through Celite. The filtrate was added in portions to a stirred slurry of 1600 ml of ethanol, 240 ml of water, 128 ml of diethyl malonate and 150 g of anhydrous sodium acetate, at 0°–3° C. The mixture was stirred and allowed to warm to room temperature (four hours), stirred at room temperature for 18 hours, then extracted with methylene chloride. The methylene chloride and ethanol were evaporated from the extract phase. The residue was dissolved in methylene chloride, the solution was washed with water, then brine, dried ($MgSO_4$), filtered, and the solvent was evaporated. The residue was stripped in a kugelrohr apparatus to 100° C./0.5 Torr. The residue was crystallized from ethauol/pentane, then recrystallized from petroleum ether to give diethyl ((2-ethylphenyl)hydrazono)malonate (53A), as a yellow solid, m.p.: 33°–34° C.

48 ml of 2 N aqueous sodium hydroxide solution was added over 15 minutes to a stirred, refluxing mixture of 22.5 g of 53A in 48 ml of ethanol. A further 192 ml of 1 N aqueous sodium hydroxide solution was added over 20 minutes to the gently refluxing mixture. Then the mixture was filtered through Celite, and the filtrate was poured into a stirred mixture of 30 ml of concentrated hydrochloric acid, 90 ml of water and about 100 g of ice. The mixture was filtered. The solid was washed with water, dried under reduced pressure, and dissolved in methylene chloride. The solution was dried ($MgSO_4$), filtered and stripped of solvent under reduced pressure. The residue was recrystallized from ethanol/water, and dissolved in methylene chloride. The solution was dried ($MgSO_4$) and the solvent was evaporated to give ((2-ethylphenyl)hydrazono)malonic acid (53B), as a solid, m.p.: 135°–136° C. (with decomposition).

One equivalent of thionyl chloride was added drop-by-drop (over two minutes) to a stirred suspension of 5.58 g of 53B in 30 ml of 1,2-dichloroethane and 3 drops of dry dimethylformamide (DMF), under nitrogen at room temperature. The mixture was allowed to stand overnight at room temperature, then refluxed for 2.5 hours, cooled to 0° C. and filtered. The solid was washed with pentane, dried and recrystallized from cyclohexane to give ((2-ethylphenyl)hydrazonO)-malonyl dichloride (53C), as a yellow solid, m.p.: 140°–141° C. (with decomposition). 53C also was prepared by treating 53B with phosphorus trichloride in chloroform.

16.4 g of titanium tetrachloride was added to a stirred solution of 22.5 g of 53C in 160 ml of chlorobenzene, under nitrogen, at 20° C. The mixture was heated at 90°–100° C. for 5 hours and let stand over a weekend at room temperature. Then 20 ml of a solution of 26.4 g of sodium hydroxide in 330 ml of water was added, drop-by-drop, and the mixture was stirred well and stripped of solvent to form a mush. The remainder of the sodium hydroxide solution was added, and the mixture was stirred and filtered through Celite. The filtrate was acidified with 12 N hydrochloric acid and filtered. The solid was dried under reduced pressure and dissolved in 150 ml of 2 N aqueous ammonium hydroxide solution. The solution was filtered. The filtrate was acidified with 12 N hydrochloric acid and filtered. The solid was washed with water, dried under reduced pressure and dissolved in warm ethanol. The solution was filtered and the solvent was evaporated from the filtrate, to give 8-methyl-4-hydroxy-cinnoline-3-carboxylic acid (53D), as a solid, m.p.: 230° C. (with decomposition).

A mixture of 0.7 g of 53D and 2.8 g of benzophenone was heated at 180°–210° C. until no more gas evolved (30 minutes). The mixture was cooled to 0° C., diluted with ether and filtered. The solid was slurried with hot 5 N aqueous sodium hydroxide solution and filtered. The filtrate was acidified with 12 N hydrochloric acid, allowed to cool and stand overnight at room temperature, and filtered. The resulting solid was dried under reduced pressure, and flash chromatographed on silica gel, using a 1:1 v:v mixture of ethyl acetate and methylene chloride as eluent, to give 8-ethyl-4-hydroxycinnoline (53E), as a solid, m.p.: 160°–161° C.

4.0 g of 53E was added in portions to stirred 20 ml of phosphorus oxychloride at 29°–32° C. The mixture was stirred for 15 minutes, quenched in ice water, and adjusted to pH 5–6 with sodium bicarbonate and saturated aqueous potassium bicarbonate solution, and extracted with ether. The extract phase was washed with brine, dried (MgSO$_4$), filtered and stripped of solvent. The unstable residue was immediately dissolved in 60 ml of dry dimethylformamide. 3.1 g of sodium p-toluenesulfinate was added to the stirred solution at 0° C. under nitrogen, then the stirred mixture was allowed to warm slowly to room temperature and stirred overnight. 200 mg more of the sodium salt was added, the mixture was stirred vigorously at 35° C. for 3 hours, and another 300 mg of the sodium salt was added. The mixture was stirred at 35° C. for 7 hours, then over a weekend at room temperature, poured into 400 ml of water, and extracted with ethyl acetate. The extract phase was washed with water, then brine, dried (MgSO$_4$), filtered and stripped of solvent, and the residue was flash chromatographed over silica gel, using a 1:1 v:v mixture of ethyl acetate and hexane as eluent, to give 4-(p-toluenesulfonyl)-8-ethylcinnoline (53F), as a solid, m.p.: 133°–134° C.

1.0 g of potassium cyanide was added to a stirred solution of 4.4 g of 53F in 60 ml of dry DMF at room temperature, under nitrogen. The mixture was stirred overnight at room temperature, under nitrogen, then 200 mg potassium cyanide was added and the mixture was stirred for 5 hours at room temperature. The mixture was quenched in water and filtered. The solid was dissolved in ethyl acetate, the solution was washed with water, dried (MgSO$_4$), filtered and stripped of solvent, to give 4-cyano-8-ethylcinnoline (53G), as a yellow solid, m.p.: 102°–104° C., with decomposition.

1.4 g of 53G was dissolved in 60 ml of 50% aqueous sulfuric acid and the mixture was stirred at 90°–100° C. for 32 hours. The mixture was cooled and made basic with 50% aqueous potassium hydroxide solution, then filtered. The filtrate was extracted with ether. The aqueous phase was acidified with 12 N hydrochloric acid and filtered. The resulting solid was dissolved in ethyl acetate, the solution was dried and stripped of solvent to give 53, as a solid, m.p.: 175°–176° C. (with decomposition).

EXAMPLE 54

Methyl 8-ethylcinnoline-4-carboxylate (54)

A solution of 1.1 g of 53, 70 ml of dry THF and 0.98 g of CDII was stirred under nitrogen at room temperature until no more gas evolved (4 hours), 0.35 g of methanol and 0.03 g of sodium acetate were added and the mixture was stirred at room temperature for 3 hours. The THF was evaporated, the residue was dissolved in methylene chloride, the solution was washed with water, dried (MgSO$_4$) and stripped of solvent. The residue was recrystallized from hexane to give 54, as a yellow solid, m.p.: 59°–60° C.

EXAMPLES 55 AND 56

2,2,2-trichloroethyl 8-methylcinnoline-4-carboxylate (55) was prepared, as a yellow solid, m.p.: 116°–118° C., with decomposition, and ethyl 8-methylcinnoline-4-carboxylate (56) was prepared, as a yellow solid, m.p.: 65°–66° C., by treating 49 with CDII and the appropriate alcohols, according to the procedures described in Example 50 for preparing 50 from 49.

EXAMPLE 57

Methyl 8-isopropylcinnoline-4-carboxylate (57), was prepared, as a yellow oil, from 2-isopropylaniline by the procedures described in Example 53 and 54 for preparing 54 from 2-ethylaniline.

EXAMPLE 58

Methyl 8-(fluoromethyl)cinnoline-4-carboxylate (58)

To 4.3 g of 50 in 1900 ml of carbon tetrachloride a few milligrams of benzoyl peroxide was added, followed by 3.2 g of N-bromosuccinimide and the stirred mixture was refluxed and irradiated with a 200-watt tungsten lamp for 6 hours. The resulting mixture was cooled, washed with water, then with very dilute aqueous sodium bicarbonate solution, dried (MgSO$_4$) and stripped of solvent. The residue (methyl 8-(bromomethyl)cinnoline-4-carboxylate) (58A) was dissolved in 80 ml of acetone, 2.11 g of lithium chloride was added, and the mixture was stirred at room temperature over a weekend. The mixture was stripped of solvent and the residue was dissolved in methylene chloride. The solution was washed with water, dried (MgSO$_4$) and stripped of solvent. The residue was flash chromatographed over silica gel, first using methylene chloride as eluent, then a 1:99 v:v mixture of ethyl acetate and methylene chloride as eluent, to give methyl 8-(chloromethyl)cinnoline-4-carboxylate (58B), as a solid, m.p.: 111°–112° .C. (with decomposition).

A mixture of 0.35 g of 58B, 3.0 g of Amberlyst A26 fluoride resin and 5 ml of benzene was stirred vigorously at mild reflux in a nitrogen atmosphere overnight. The resulting mixture was filtered, and the filtrate was stripped of solvent. The residue was chromatographed over silica gel, using a 1:99 v:v mixture of ethyl acetate and methylene chloride as eluent, to give 58, as a yellow solid, m.p.: 104°–105° C.

EXAMPLE 59

Methyl 6,7-dimethylcinnoline-4-carboxylate (59)

95 ml of acetic anhydride was added to a stirred solution of 3,4-dimethylaniline in 300 ml of glacial acetic acid at such a rate that the temperature of the mixture slowly rose to 60° C. The resulting mixture was stirred while the temperature dropped to room temperature, then evaporated to dryness. A mixture of water and ice was added to the residue, followed by methylene chloride. The resulting mixture was stirred and treated with solid sodium bicarbonate until neutral. The organic phase was separated, and dried (MgSO$_4$), and the solvent was evaporated to give 3,4-dimethylacetanilide (59A).

105 ml of acetyl chloride was added to a solution of 130 g of 59A in 1040 ml of carbon disulfide, then 410 g of aluminum chloride was slowly added to the stirred mixture. The mixture was stirred at reflux for 1.5 hours, cooled and the carbon disulfide phase was decanted. The remainder was poured onto ice, and the resulting precipitate was collected, washed with water and dried to give 2-acetyl-4,5-dimethylacetanilide (59B).

A mixture of 44 g of 59B and 300 ml of concentrated hydrochloric acid was refluxed for 30 minutes, then cooled in an ice bath and filtered. The collected solids were partitioned between methylene chloride and a saturated aqueous solution of sodium bicarbonate. The methylene chloride phase was separated and dried ($MgSO_4$), and the solvent was evaporated under reduced pressure. The residue was recrystallized from a 2:1 v:v mixture of hexane and ethyl acetate to give 2-amino-4,5-dimethylacetophenone (59C).

10.5 g of 59C was dissolved in 30 ml of concentrated hydrochloric acid was kept cold with an ice bath, then 50 ml of water was added and the resulting mixture was treated at about 0° C. with sodium nitrite until the diazotation was complete by iodine-starch reaction. The resulting mixture was poured onto an ice-cold mixture of 50 g of sodium acetate, 150 ml of water, 50 g of ice and 50 ml of methylene chloride, and the mixture was stirred overnight, spontaneously warming to room temperature. The resulting mixture was filtered, the collected solid was washed with methylene chloride, then water, and dried in a vacuum oven. The product was recrystallized from ethanol to give 6,7-dimethyl-4-hydroxycinnoline (59D), as orange crystals, m.p.: above 260° C. Further 59D was obtained by adding petroleum ether to the mother liquor from the recrystallization.

59D was converted to 59, obtained as a yellow solid, m.p.: 119°–120° C. (with decomposition), by treating 59D according to the procedures described in Example 53 for converting 53E to 53.

EXAMPLE 60

7,8-dimethylcinnoline-4-carboxylic acid (60)

60 was prepared, as a gold-colored solid, m.p.: 189° C. (with decomposition) from 7,8-dimethyl-4-hydroxycinnoline (60A), according to the procedures described in Example 53 for preparing 53 from 53E. 60A was prepared as follows:

22.3 ml of concentrated hydrochloric acid was added drop-by-drop to a stirred suspension of 2-amino-3,4-diemthylacetophenone (A. Brandstrom and S. A. I. Carlson, Acta Chemica Scandinavica, volume 21, pages 983–992 (1967)), 100 ml of water and 100 g of ice at 0° C. The resulting mixture was stirred at 0° C. for 15 minutes, then a solution of 7.8 g of sodium nitrite in 60 ml of water was added drop-by-drop over 2 minutes, at 0° C. The mixture was stirred for 40 minutes at 0° C., then 200 ml of ice-cold methylene chloride and 200 ml of an ice-cold aqueous solution containing 81.5 g of sodium acetate were added. The mixture was stirred for 6 hours at 0° C., allowed to warm gradually to room temperature, then filtered. The collected solid was dried by azeotroping with toluene and recrystallized from ethanol-hexane to give 60A, as a tan solid, m.p.: above 260° C.

EXAMPLE 61

Methyl 7-methylcinnoline-4-carboxylate (61)

7-Methyl-4-hydroxycinnoline (61A) was prepared from 3-methylaniline by the procedures described in Example 53 for preparing 53E from 2-ethylaniline. 61A was converted to 61, obtained as a yellow solid, m.p.: 114°–115° C., by the procedures described in Example 53 and 54 for preparing 53 from 53E.

EXAMPLE 62

6,7-dimethylcinnoline-4-carboxylic acid (62)

0.95 g of 6,7-dimethyl-4-cinnolinecarbonitrile (obtained as an intermediate in the preparation of 59) was mixed with 50 ml of a 50% aqueous solution of sulfuric acid, and the mixture was stirred at 90°–100° C. overnight. The resulting mixture was made basic with 50% aqueous sodium hydroxide solution and filtered. The filtrate was extracted with ether. The remaining aqueous phase was acidified with 12N hydrochloric acid and extracted with ethyl acetate. The extract was dried ($MgSO_4$) and stripped of solvent to give 62, as a yellow solid, m.p.: 204°–205° C. (with decomposition).

EXAMPLES 63–70

The following esters were prepared from 49 and the corresponding alcohols by the procedures described in Example 5 for preparing 5 from 1:

2-pyridinylmethyl ester (63), as a yellow solid, m.p.: 132°–133° C.;

2,2-(dimethoxy)ethyl ester (64), as a yellow solid, m.p.: 72°–73° C.;

1,3-dioxolan-4-ylmethyl ester (65), as a yellow solid, m.p.: 100°–101° C.;

1,3-dioxan-5-yl ester (66), as a yellow solid, m.p.: 138°–139° C.;

2-(2-ethoxyethoxy)ethyl ester (67), as a yellow oil;

oxiranylmethyl ester (68), as a yellow solid, m.p.: 65°–67° C.;

2-(2-methoxyethoxy)ethyl ester (69), as a yellow solid, m.p.: 42°–43° C.;

2-(methoxy)ethyl ester (70), as a yellow solid, m.p.: 75°–76° C.

EXAMPLES 71 AND 72

By similar procedures, the 2,2-(dimethoxy)ethyl esters of 53 and 57 were prepared, as a yellow solid (71), m.p.: 33°–34° C., and a yellow liquid (72) respectively.

EXAMPLE 73

The 2-(ethoxy)ethyl ester of 49 was prepared as a yellow oil (73) from 49 and 2-(ethoxy)ethanol by the procedures described in Example 42 for preparing 42 from 1.

EXAMPLE 74

The methyl ester of 60 was prepared as yellow needles (74), m.p.: 95°–96° C., from 60 and methanol, according to the procedures described in Example 45 for preparing 45 from 1.

EXAMPLE 75

The 2-N-oxide of 50 was prepared, as a yellow solid (75), m.p.: 145°–147° C., by oxidation of 50, by the procedure described in Example 31 for preparing 31 from 8.

EXAMPLE 76

Carboxymethyl Cinnoline-4-carboxylate Isopropylamine Salt (76)

A solution of 2.4 g of 19 in 150 ml of methanol containing 0.75 g of 5% palladium-on-carbon catalyst was hydrogenated (40 psig.) for 19 hours. The resulting mixture was filtered, and stripped of solvent. The residue was dissolved in an excess of isopropylamine, then the amine was evaporated from the solution under reduced pressure, to give 76, as tan crystals, m.p.: 173° C. (with decomposition).

Compounds of Formula I have been found to adversely affect the growth of some plants, many of which are commonly considered as weeds, and therefore to be useful for controlling the growth of such unwanted plants. Compounds of Formula I have been found to have selectivity with respect to some crop plants—i.e., they control weeds at dosages at which they do not significantly harm the crop plants. While compounds of Formula I appear to have some activity when applied preemergence or preplant incorporated (applied to the soil before the seeds have sprouted), most appear to be more effective when applied postemergence (applied to the foliage of the growing plant).

Accordingly, the invention includes a method of combatting unwanted plants which comprises applying to the locus an effective amount of a compound of Formula I. In the cases where it is desired to control weeds in crop plantings, it is of course preferable to employ the lowest dosage that will control the weeds, for this will minimize any possible deleterious effect of the compound upon the crop plants.

For application, the compound of Formula I ordinarily is applied most effectively by formulating it with a suitable inert carrier or surface-active agent, or both. The invention, therefore, also includes compositions suitable for combatting unwanted plants, such compositions comprising an inert carrier or surface-active agent, or both, and as active ingredient at least one compound of Formula I.

The term "carrier" as used herein means an inert solid or liquid material, which may be inorganic or organic and of synthetic or natural origin, with which the active compound is mixed or formulated to facilitate its application to the plant, seed, soil or other object to be treated, or its storage, transport and/or handling. Any of the materials customarily employed in formulating pesticides, herbicides, or fungicides, are suitable.

Suitable solid carriers are natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as, for example, carbon and sulfur; natural and synthetic resins such as, for example, coumarone resins, polyvinyl chloride and styrene polymers and copolymers; hitumen; waxes such as, for example, beeswax, paraffin wax, and chlorinated mineral waxes; solid fertilizers, for example, superphosphates; and ground, naturally-occurring, fibrous materials, such as ground corncobs.

Examples of suitable liquid carriers are water, alcohols such as isopropyl alcohol and glycols; katones such as acetone, methyl ethyl ketone, methyl isobutyl ketone and cyclohexanone; ethers such as cellosolves; aromatic hydrocarbons such as benzene, toluene and xylene; petroleum fractions such as kerosene, light mineral oils; chlorinated hydrocarbons such as carbon tetrachloride, perchloroethylene and trichloromethane. Also suitable are liquefied, normally vaporous and gaseous compounds. Mixtures of different liquids are often suitable.

The surface-active agent may be an emulsifying agent or a dispersing agent or a wetting agent; it may be nonionic or ionic. Any of the surface-active agents usually applied in formulating herbicides or insecticides may be used. Examples of suitable surface-active agents are the sodium and calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; condensates of these with ethylene oxide and/or propylene oxide; condensation products of fatty alcohols or alkyl phenols, for example, p-octyl-phenol or p-octylcresol, with ethylene oxide and/or propylene oxide; sulfates or sulfonates of these condensation products, alkali or alkaline earth metal salts, preferably sodium salts, of sulfuric or sulfonic acid esters containing at least 10 carbon atoms in the molecule, for example, sodium lauryl sulfate, sodium secondary alkyl sulfates, sodium salts of sulfonated castor oil, and sodium alkylaryl sulfonates such as sodium dodecylbenzene sulfonate; and polymers of ethylene oxide and copolymers of ethylene oxide and propylene oxides.

The compositions of the invention may be prepared as wettable powders, dusts, granules, solutions, emulsifiable concentrates, emulsions, suspension concentrates and aerosols. Wettable powders are usually compounded to contain 25 to 75% by weight of active compound and usually contain, in addition to the solid carrier, 3-10% by weight of a dispersing agent, 2-15% of a surface-active agent and, where necessary, 0-10% by weight of stabilizer(s) and/or other additives such as penetrants or stickers. Dusts are usually formulated as a dust concentrate having a similar composition to that of a wettable powder but without a dispersant or surface-active agent, and are diluted in the field with further solid carrier to give a composition usually containing 0.5-10% by weight of the active compound. Granules are usually prepared to have a size between 10 and 100 BS mesh (1.676-0.152 mm), and may be manufactured by agglomeration or impregnation techniques. Generally, granules will contain 0.5-25% by weight of the active compound, 0-1% by weight of additives such as stabilizers, slow release modifiers and binding agents. Emulsifiable concentrates usually contain, in addition to the solvent and, when necessary, cosolvent, 10-50% weight per volume of the active compound, 2-20% weight per volume emulsifiers and 0-20% weight per volume of appropriate additives such as stabilizers, penetrants and corrosion inhibitors. Suspension concentrates are compounded so as to obtain a stable, non-sedimenting, flowable product and usually contain 10-75% weight of the active compound, 0.5-5% weight of dispersing agents, 1-5% of surface-active agent, 0.1-10% weight of suspending agents, such as defoamers, corrosion inhibitors, stabilizers, penetrants and stickers, and as carrier, water or an organic liquid in which the active compound is substantially insoluble; certain organic solids or inorganic salts may be dissolved in the carrier to assist in preventing sedimentation or as antifreeze agents for water.

Of particular interest in current practice are water-dispersible granular formulations. These are in the form of dry, hard granules that are essentially dust-free, and are resistant to attrition on handling, thus minimizing the formation of dust. On contact with water, the granules readily disintegrate to form stable suspensions of the particles of active material. Such formulations contain 90% or (up to 95%) more by weight of finely divided active material, 3–7% by weight of a blend of surfactants, which act as wetting, dispersing, suspending and binding agents, and may contain up to 3% by weight of a finely divided carrier, which acts as a resuspending agent.

Aqueous dispersions and emulsions, for example, compositions obtained by diluting a wettable powder or a concentrate according to the invention with water, also lie within the scope of the present invention. The said emulsions may be of the water-in-oil or of the oil-in-water type, and may have thick, mayonnaise-like consistency.

It is evident from the foregoing that this invention contemplates compositions containing as little as about 0.5% by weight to as much as about 95% by weight of a compound of Formula I as the active ingredient.

The compositions of the invention may also contain other ingredients, for example, other compounds possessing pesticidal, especially insecticidal, acaricidal, herbicidal or fungicidal properties, as are appropriate to the intended purpose.

Protection of a locus or area from undesirable plants is effected by applying a compound of Formula I, ordinarily in a composition of one of the aforementioned types, to sail in which the seeds of the unwanted plants are present, or to the foliage of the unwanted plants. The active compound, of course, is applied in an amount sufficient to exert the desired action.

The amount of the compound of the invention to be used in combatting undesired plants will naturally depend on the condition of the plants, the degree of activity desired, the formulation used, the mode of application, the climate, the season of the year, and other variables. Recommendations as to precise amounts are, therefore, not possible. In general, however, application to the locus to be protected of from 0.1 to 10.0 kg per hectare of the compound of Formula I will be satisfactory.

EXAMPLES OF ACTIVITY WITH RESPECT TO PLANTS

PRIMARY TESTS

In the following examples, the species of plants that were tested were:
Barnyardgrass (watergrass)—*Echiuochloa crus-galli,*
Large crabgrass—*digitaris sangulnalis,*
Downy brome—*Bromus tectorum,*
Yellow foxtail—*Setaria lutescens,*
Redroot pigweed—*Amaranthus retroflexus,*
Sicklepod—*Cassia obtusifolia,*
Velvetleaf—*Aburtion theophrasti,*
Garden cress—*Lepidium sativum,*
Johnson grass—*Sorghum halepense,*
Morninggloty—*Ipomoea sp.*

TEST PROCEDURES

The preemergence (soil) herbicidal activity of compounds of Formula I was evaluated by planting seeds of barnyardgrass, garden cress, downy brome, velvetleaf, yellow foxtail, and sicklepod or morningglory in test tubes, nominally measuring 25×200 millimeters, filled about three-quarters full of untreated soil, in each case covered on top with about 2.5 cubic centimeters of soil treated with a certain amount of the test compound. The treated soil applied to the tubes containing the barnyardgrass and cress seeds contained one milligram of the test compound per tube, and contained 0.1 milligram of the test compound per each tube containing the seeds of the other plants. The dosages were approximately 20 and 2.0 pounds of test compound per acre, respectively. The seeds were planted on top of the treated soil and covered with about 1.5 cubic centimeters of untreated soil. The planted soil was held under controlled conditions of temperature, moisture, and light for 9 to 10 days. The amounts of germination and growth in each tube were evaluated on a 0 to 9 scale, the numeric ratings having the following meanings:

| Rating | Meaning |
| --- | --- |
| 9 | No living tissue |
| 8 | Plant severely damaged and expected to die |
| 7 | Plant badly damaged, but expected to live |
| 6 | Moderate damage, but complete recovery expected |
| 5 | Intermediate damage (probably unacceptable for crop plants) |
| 3–4 | Observable damage |
| 1–2 | Plant slightly affected, possibly by the chemical, possibly due to biological variability |
| 0 | No visible effect |

The postemergence (foliar) herbicidal activity of compounds of Formula I was evaluated by spraying 10-day-old large crabgrass plants, 13-day-old pigweed plants, 6-day-old johnsongrass plants, 9-day-old velvetleaf plants, 9-day-old yellow foxtail plants and either 9-day-old sicklepod plants or 5-day-old morningglory plants to runoff with a liquid formulation of the test compound. The crabgrass and pigweed plants were sprayed with 2.4 millititers of a 0.25% solution (about ten pounds of the test compound per acre), and other plants were sprayed with 2.4 millititers of a 0.025% solution (about one pound of the test compound per acre). The sprayed plants were held under controlled conditions of temperature, moisture and light for 7 to 8 days, when the effect of the test compound was evaluated visually, the results being rated on the 0 to 9 scale described above.

Results of the preemergence and postemergence herbicidal activity tests are set forth in Table I.

TABLE I

| | HERBICIDAL ACTIVITY | | | | | | | | | | | | | |
| --- | --- | --- | --- | --- | --- | --- | --- | --- | --- | --- | --- | --- | --- | --- |
| | Preemergence | | | | | | | Postemergence | | | | | | |
| Compound | Barnyardgrass | Garden Cress | Downy Brome | Velvetleaf | Yellow foxtail | Sicklepod | Morningglory | Crabgrass | Pigweed | Johnsongrass | Velvetleaf | Yellow Foxtail | Sicklepod | Morning glory |
| 1 | 3 | 6 | 3 | 0 | 7 | 3 | | 7 | 5 | 0 | 2 | 9 | 2 | |
| 2 | 2 | 2 | 2 | 0 | 8 | 2 | — | 9 | 4 | 1 | 2 | 9 | 2 | — |

TABLE I-continued

| | HERBICIDAL ACTIVITY | | | | | | | | | | | | |
|---|---|---|---|---|---|---|---|---|---|---|---|---|
| | Preemergence | | | | | | Postemergence | | | | | | |
| Compound | Barnyard-grass | Garden Cress | Downy Brome | Velvet-leaf | Yellow foxtail | Sickle-pod | Morning-glory | Crab-grass | Pig-weed | Johnson-grass | Velvet-leaf | Yellow Foxtail | Sickle pod | Morning glory |
| 3 | 2 | 6 | 0 | 0 | 9 | 0 | — | 9 | 4 | 0 | 1 | 9 | 2 | — |
| 4 | 3 | 4 | 0 | 0 | 8 | 2 | — | 9 | 5 | 0 | 2 | 9 | 2 | — |
| 5 | 0 | 2 | 2 | 0 | 8 | 3 | — | 9 | 6 | 1 | 2 | 9 | 3 | — |
| 6 | 0 | 2 | 0 | 0 | 8 | 0 | — | 9 | 6 | 0 | 2 | 9 | 3 | — |
| 7 | 0 | 7 | 0 | 2 | 8 | 0 | — | 9 | 6 | 0 | 2 | 8 | 2 | — |
| 8 | 0 | 5 | 0 | 0 | 8 | 3 | — | 5 | 8 | 0 | 2 | 5 | 2 | — |
| 9 | 0 | 0 | 0 | 0 | 8 | 0 | — | 7 | 5 | 1 | 2 | 9 | 3 | — |
| 10 | 2 | 3 | 0 | 0 | 8 | 2 | — | 8 | 5 | 0 | 0 | 9 | 0 | — |
| 11 | 2 | 3 | 0 | 0 | 8 | 2 | — | 6 | 5 | 0 | 2 | 9 | 2 | — |
| 12 | 2 | 2 | 0 | 0 | 8 | 0 | — | 8 | 5 | 0 | 0 | 9 | 2 | — |
| 13 | 0 | 0 | 0 | 0 | 9 | 0 | — | 5 | 0 | 1 | 0 | 9 | 2 | — |
| 14 | 0 | 0 | 0 | 0 | 9 | 0 | — | 9 | 4 | 0 | 0 | 9 | 3 | — |
| 15 | 0 | 0 | 0 | 0 | 8 | 0 | — | 7 | 6 | 0 | 0 | 9 | 2 | — |
| 16 | 0 | 0 | 0 | 0 | 8 | 0 | — | 6 | 5 | 0 | 0 | 9 | 2 | — |
| 17 | 2 | 2 | 0 | 0 | 9 | 0 | — | 7 | 5 | 0 | 0 | 9 | 3 | — |
| 18 | 2 | 4 | 0 | 0 | 8 | 0 | — | 7 | 6 | 0 | 2 | 9 | 2 | — |
| 19 | 0 | 0 | 0 | 0 | 7 | — | 2 | 8 | 6 | 0 | 0 | 9 | — | 4 |
| 20 | 0 | 0 | 0 | 0 | 7 | — | 0 | 7 | 5 | 0 | 2 | 9 | — | 3 |
| 21 | 0 | 0 | 0 | 0 | 0 | — | 0 | 9 | 7 | 3 | 2 | 9 | — | 2 |
| 22 | 3 | 3 | 2 | 2 | 8 | — | 4 | 9 | 5 | 0 | 2 | 9 | — | 3 |
| 23 | 0 | 0 | 0 | 0 | 0 | — | 0 | 6 | 6 | 0 | 0 | 9 | — | 2 |
| 24 | 0 | 6 | 0 | 0 | 0 | — | 0 | 4 | 3 | 0 | 0 | 9 | — | 4 |
| 25 | 0 | 0 | 0 | 0 | 0 | — | 0 | 4 | 2 | 3 | 0 | 8 | — | 5 |
| 26 | 0 | 0 | 0 | 0 | 8 | — | 0 | 7 | 4 | 0 | 2 | 9 | — | 5 |
| 27 | 0 | 0 | 0 | 0 | 6 | 0 | — | 5 | 5 | 0 | 0 | 9 | 3 | — |
| 28 | 0 | 0 | 0 | 0 | 8 | 0 | — | 4 | 4 | 0 | 0 | 8 | 3 | — |
| 29 | 0 | 0 | 0 | 0 | 9 | 0 | — | 5 | 4 | 0 | 0 | 9 | 0 | — |
| 30 | — | — | 0 | 0 | 3 | 0 | 0 | 5 | 4 | 0 | 0 | 9 | 4 | 5 |
| 31 | 0 | 3 | 2 | 0 | 9 | 0 | — | 2 | 3 | 0 | 0 | 7 | 0 | — |
| 32 | 0 | 0 | 0 | 0 | 0 | 0 | — | 8 | 6 | 0 | 2 | 9 | 2 | — |
| 33 | 0 | 0 | 0 | 0 | 8 | — | 0 | 9 | 5 | 0 | 0 | 9 | — | 0 |
| 34 | 2 | 6 | 0 | 3 | 7 | — | 2 | 5 | 3 | 0 | 0 | 9 | — | 0 |
| 35 | 4 | 3 | 0 | 0 | 9 | — | 3 | 7 | 3 | 0 | 0 | 9 | — | 6 |
| 36 | 0 | 0 | 0 | 0 | 8 | — | 8 | 8 | 5 | 2 | 0 | 9 | — | 3 |
| 37 | 3 | 0 | 0 | 0 | 9 | — | 7 | 5 | 6 | 0 | 0 | 9 | — | 0 |
| 38 | 5 | 7 | — | 3 | 8 | 0 | — | 5 | 7 | 2 | 2 | 8 | 2 | — |
| 39 | 2 | 3 | 0 | 0 | 8 | 0 | — | 9 | 3 | 0 | 2 | 9 | 2 | — |
| 40 | 0 | 0 | 0 | 0 | 0 | 0 | — | 9 | 2 | 2 | 0 | 9 | 2 | — |
| 42 | — | — | 0 | 0 | 9 | 0 | 0 | 9 | 0 | 0 | 0 | 9 | 0 | 9 |
| 43 | — | — | 0 | 0 | 9 | 0 | 0 | 9 | 0 | 3 | 0 | 8 | 0 | 8 |
| 44 | — | — | 0 | 0 | 9 | 0 | 0 | 9 | 0 | 6 | 0 | 9 | 0 | 8 |
| 45 | — | — | 0 | 7 | 9 | 0 | 0 | 9 | — | 3 | 0 | 9 | 0 | 9 |
| 46 | — | — | 0 | 9 | 9 | 0 | 2 | 9 | — | 0 | 0 | 9 | 0 | 9 |
| 47 | — | — | 0 | 0 | 8 | 0 | 0 | 9 | — | 3 | 0 | 9 | 0 | 9 |
| 48 | — | — | 0 | 0 | 9 | 0 | 4 | 9 | — | 3 | 2 | 9 | 0 | 9 |
| 49 | 0 | 6 | 0 | 2 | 6 | — | 5 | 3 | 6 | 3 | 3 | 3 | — | 4 |
| 50 | 0 | 0 | 0 | 0 | 0 | — | 0 | 7 | 2 | 2 | 0 | 9 | — | 2 |
| 51 | 0 | 0 | 0 | 0 | 0 | 0 | — | 9 | 3 | 2 | 0 | 8 | — | 2 |
| 52 | 0 | 0 | 0 | 0 | 0 | — | 0 | 9 | 2 | 2 | 0 | 8 | — | 3 |
| 53 | 0 | 7 | 0 | 3 | 6 | — | 4 | 3 | 4 | 0 | 4 | 4 | — | 2 |
| 54 | 0 | 0 | 0 | 0 | 0 | — | 0 | 6 | 6 | 2 | 2 | 6 | — | 9 |
| 55 | 0 | 2 | 0 | 0 | 3 | — | 0 | 2 | 0 | 1 | 0 | 6 | — | 2 |
| 56 | 0 | 0 | 0 | 0 | 3 | — | 3 | 4 | 9 | 2 | 4 | 6 | — | 2 |
| 57 | 0 | 3 | 0 | 0 | 0 | — | 0 | 8 | 9 | 0 | 2 | 5 | — | 0 |
| 58 | — | — | 0 | 0 | 6 | 0 | 0 | 5 | 0 | 2 | 0 | 9 | 0 | 3 |
| 59 | 2 | 3 | 0 | 2 | 0 | — | 3 | 6 | 5 | 2 | 3 | 7 | — | 2 |
| 60 | 2 | 3 | 0 | 0 | 0 | — | 0 | 0 | 0 | 0 | 0 | 9 | — | 0 |
| 61 | 0 | 2 | 0 | 0 | 0 | — | 0 | 3 | 2 | 0 | 0 | 7 | — | 0 |
| 62 | 0 | 0 | 0 | 0 | 0 | — | 0 | 0 | 0 | 0 | 0 | 7 | — | 0 |
| 63 | 0 | 0 | 0 | 0 | 0 | — | 0 | 4 | 2 | 0 | 2 | 9 | — | 2 |
| 64 | — | — | 0 | 0 | 0 | — | 0 | 9 | 3 | 0 | 4 | 9 | 2 | 9 |
| 65 | — | — | 0 | 0 | 0 | 0 | 0 | 7 | 0 | 3 | 4 | 9 | 0 | 0 |
| 66 | — | — | 0 | 0 | 0 | 0 | 0 | 6 | 0 | 0 | 4 | 9 | 0 | 9 |
| 67 | — | — | 0 | 0 | 5 | 0 | 0 | 8 | 0 | 3 | — | 9 | 0 | 8 |
| 68 | — | — | 0 | 0 | 0 | 0 | 0 | 7 | 0 | 6 | 3 | 8 | 0 | 8 |
| 69 | — | — | 0 | 0 | 0 | 0 | 0 | 7 | 0 | 0 | 0 | 9 | 0 | 9 |
| 70 | — | — | 0 | 0 | 0 | 0 | 0 | 8 | 0 | 3 | 3 | 9 | 2 | 9 |
| 71 | — | — | 0 | 0 | 0 | 0 | 0 | 9 | 2 | 2 | 2 | 9 | 2 | 8 |
| 72 | — | — | 0 | 0 | 0 | 0 | 0 | 5 | 2 | 0 | 2 | 9 | 0 | 8 |
| 73 | — | — | 0 | 0 | 0 | 0 | 0 | 8 | 0 | 0 | 3 | 9 | 2 | 9 |
| 74 | 0 | 0 | 0 | 0 | 0 | — | 0 | 3 | 4 | 0 | 0 | 7 | — | — |
| 75 | 0 | 0 | 0 | 0 | 0 | — | 0 | 0 | 0 | 0 | 0 | 6 | — | — |
| 76 | 4 | 3 | 3 | 2 | 8 | — | 3 | 9 | 4 | 0 | 0 | 9 | — | 3 |

SECONDARY TESTS

In the following examples, the species of plants that were tested were:
Barnyardgrass,
Downy Brome,
Johnsongrass,
Wild oats—*Avena fatua,*
Yellow foxtail,
Goose grass—*Eleusine indica,*
Yellow nutsedge—*Cyperus esculentus,*
Cocklebur—*Xanthium pennsylvanicum,*
Morningglory,
Wild mustard—*Brassica kaber,*
Redroot pigweed,
Sicklepod,
Velvetleaf,
Corn—*Zea mays,*
Cotton—*Gossypium hirsutum,*
Rice—*Oryza sativa,*
Grain sorghum—*Sorghum vulgare,*
Soybeans—*Glycine max,*
Sugarbeets—*Beta vulgaris,*
Wheat—*Triticum aestivum,*
Nightshade—*Solarium* sp.

TEST PROCEDURES

The preemergence activity of compounds of Formula I was further determined with respect to certain species of crop plants and common species of weeds, by spraying a formulation of the test compound on soil in small pots in which seeds of the plants had been sown. The postemergence herbicidal activity of compounds of Formula I was evaluated with respect to the crop plants and weeds, by spraying a formulation of the test compound on the follage of the young growing plants. In each series of tests, the plants were grown in pots placed in narrow trays and sprayed with the formulation. Dosages of the test compounds of 4.0 pounds/acre in some cases, and 1.0 at 0.25 pound/acre in all cases, were used. The results of the tests were evaluated on the basis of the 0-9 scale described with respect to the earlier tests. Activity of the test compound in such case was characterized as follows:

|  | Dosage (lb/acre) | Rating (one or another) |
| --- | --- | --- |
| Highly active | 0.25 | 8–9 |
|  | 1.0 | 8–9 |
|  | 4.0 | 8–9 |
| Very active | 0.25 | 6–7 |
|  | 1.0 | 8–9 |
|  | 4.0 | 8–9 |
| Active | 0.25 | 4–5 |
|  | 1.0 | 5–7 |
|  | 4.0 | 7–9 |
| Slightly active | 0.25 | 2–3 |
|  | 1.0 | 3–4 |
|  | 4.0 | 4–5 |
| Essentially inactive | 0.25 | 0 |
|  | 1.0 | 0–3 |
|  | 4.0 | 1–3 |

Compounds 1–3, 11, 13, 15–18 and 37 were tested preemergence: Compound 1 was very active with respect to yellow foxtail; active with respect to rice and cocklebur; slightly active with respect to morningglory; and essentially inactive with respect to all of the other species of test plants.

Compounds 2, 3, 11, 13, 15–18 and 37 were very active with respect to yellow foxtail and essentially inactive with respect to all of the other species of the plants tested.

Compounds 1–37, 39–41, 44, 49–51, 54, 56, 57, 59–63, 69, 71, 72, 74 and 76 were tested postemergence.

With respect to yellow foxtail, Compounds 1–4, 9, 12, 15, 19–26, 28, 29, 32–36, 39, 44, 69 and 76 were highly active; Compounds 5–6, 10, 17, 18, 37, 40, 50, 51 and 72 were very active; Compounds 7, 11, 13, 14, 16, 27, 30, 49, 63 and 71 were active; and Compounds 8 and 31 were slightly active.

With respect to cocklebur, Compounds 1–6, 9, 11, 12, 15, 17, 18, 20–23, 27, 28, 32, 33, 35, 51 and 72 were highly active; Compounds 16, 19, 34, 36, 37, 39, 44, 50, 69 and 76 were very active; Compounds 13, 21, 25, 26, 29, 30, 40, 49, 54, 56, 57, 71 and 72 were active; Compounds 7, 10, 14, 24, 61 and 63 were slightly active; and Compounds 8, 10 and 31 were essentially inactive.

With respect to morningglory, Compounds 2, 3, 4, 6, 12, 32 and 36 were highly active; Compounds 9, 17, 28, 29, 34 and 37 were very active; Compounds 5, 10, 15, 16, 18, 20, 25, 33, 39, 44, 49, 50, 54, 56, 57, 69 and 76 were active; Compounds 1, 7, 11, 13, 14, 19, 24, 50, 51, 61 and 63 were slightly active; and Compounds 7, 8, 22 and 26 were essentially inactive.

With respect to nightshade, Compound 9 was very active; Compounds 3–6, 12, 13, 15–18, 20, 33, 49, 50, 54 and 56 were active; Compounds 1, 2, 7, 11, 14, 19, 21–26, 28, 30, 32, 51 and 57 were slightly active; and Compounds 8, 10, 27, 31, 32, 38, 40 and 51 were essentially inactive.

·With respect to pigweed, Compound 21 were active: Compounds 19, 22, 23, 26, 30, 39 and 62 were slightly active.

With respect to wild mustard, Compound 50 was found to be very active; Compounds 20, 33, 49, 51 and 56 were found to be active.

With respect to velvetleaf, Compounds 50 and 54 were found to be active; Compounds 22, 30, 36 and 72 were found to be slightly active.

With respect to all of the other varieties of plants, all of the compounds were essentially inactive.

The amine salts were found to have essentially the same activity as 1.

Compound 1 also was found to be very active with respect to crabgrass and field sandbur (*Cenchrus incerius*) when applied postemergence.

Compounds of Formula I also are precursors to the cinuolinium compounds of application Ser. No. 651,410, which have plant growth regulating properties which differ significantly from those of the compounds of Formula I.

We claim:

1. A method for controlling the growth of unwanted plants at a locus, which method comprises applying to the locus an effective amount of a compound of the formula

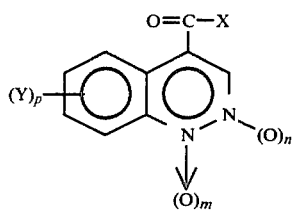

wherein m is zero or one, n is zero or one, with the proviso that at least one of m and n is zero, p is zero, one or two, with the proviso that when p is two, one of Y is methyl, or ethyl, X is one of the moieties: —NH₂, —NHNH₂, —NHOH and —O—R, wherein R is (a) hydrogen;
(b) alkyl of one to ten carbon atoms;
(c) alkyl of one to ten carbon atoms substituted by one of cyano, alkanoyl wherein the alkyl moiety contains from one to four carbon atoms, carboxy, alkoxycarbonyl wherein the alkyl moiety contains from one to four carbon atoms, aminocarbonyl, mono- and dialkylaminocarbonyl wherein the alkyl moiety contains from one to four carbon atoms, benzyloxycarbonyl, alkylthiocarbonyl wherein the alkyl moiety contains from one to four carbon atoms, alkenyl and alkynyl of two to four carbon atoms, cycloalkyl of three to six carbon atoms and phenyl optionally substituted by one or more halogen atoms, or one or two of mono- and polyhaloalkyl, car- boxy, nitro, alkoxycarbonyl, alkyl, alkoxy and alkyl- thio, wherein each alkyl moiety contains from one to four carbon atoms;
(d) alkyl of two to ten carbon atoms substituted by one to three halogen atoms (bromine, chlorine, fluorine); one of alkylthio, alkanoyloxy, mono- and dialkylamino wherein each alkyl moiety contains from one to four carbon atoms moieties of the formula $$-(-O-R^1-)_q-OR^2$$

(in which $R^1$ is alkylene of one to four carbon atoms, $R^2$ is hydrogen or alkyl of one to six carbon atoms and g is one, two, three or four), or one to four of hydroxy and alkoxy, with the proviso that in this substituted alkyl moiety the carbon atom bonded to the indicated oxygen atom is unsubstituted (—CH₂—);
(e) cycloalkyl of three to six carbon atoms;
(f) phenyl optionally substituted by one or more halogen atoms, or one or two of mono- and polyhaloalkyl, carboxy, nitro, alkoxycarbonyl, alkyl, alkoxy and alkylthio, wherein each alkyl moiety contains from one to four carbon atoms;

and Y is (a) alkyl of one to ten carbon atoms
(b) alkyl of one to ten carbon atoms substituted by one of fluorine, cyano, carboxy, alkenyl of two to four carbon atoms, benzyl, alkoxycarbonyl wherein the alkyl moiety contains from one to four carbon atoms, alkylthio wherein the alkyl moiety contains from one to four carbon atoms, alkylsulfonyl wherein the alkyl moiety contains from one to four carbon atoms, alkoxy wherein the alkyl moiety contains from one to four carbon atoms, and phenoxy, and salts of those compounds wherein R is hydrogen or X is —NHOH; said salts being those of alkali metals, alkaline earth metals, ammonia and mono-, di- and tri- alkyl- and -alkanol- amines wherein each alkyl moiety is from one to twenty carbon atoms.

* * * * *